United States Patent
Gilboa (10) Patent No.: US 6,574,498 B1
(45) Date of Patent: Jun. 3, 2003

(54) LINKING OF AN INTRA-BODY TRACKING SYSTEM TO EXTERNAL REFERENCE COORDINATES

(75) Inventor: Pinhas Gilboa, Haifa (IL)

(73) Assignee: Super Dimension Ltd., Herzelia (IL)

( * ) Notice: Subject to any disclaimer, the term of this patent is extended or adjusted under 35 U.S.C. 154(b) by 0 days.

(21) Appl. No.: 09/830,484

(22) PCT Filed: Nov. 4, 1999

(86) PCT No.: PCT/US99/26095

§ 371 (c)(1),
(2), (4) Date: Apr. 27, 2001

(87) PCT Pub. No.: WO01/06917

PCT Pub. Date: Feb. 1, 2001

Related U.S. Application Data (60) Provisional application No. 60/154,254, filed on Sep. 16, 1999.

(51) Int. Cl.$^7$ .................................................. A61B 5/00
(52) U.S. Cl. ...................................... 600/424; 600/427
(58) Field of Search ............................... 600/424, 407, 600/437, 427, 438; 128/899; 607/122

(56) References Cited

U.S. PATENT DOCUMENTS

| | | | |
|---|---|---|---|
| 5,515,853 A | | 5/1996 | Smith et al. |
| 5,558,091 A | | 9/1996 | Acker et al. |
| 5,697,377 A | | 12/1997 | Wittkampf |
| 5,840,025 A | * | 11/1998 | Ben-Haim ............... 600/424 |
| 5,868,673 A | | 2/1999 | Vesely |
| 5,899,860 A | | 5/1999 | Pfeiffer et al. |
| 5,938,602 A | * | 8/1999 | Lloyd ..................... 600/424 |
| 5,954,649 A | | 9/1999 | Chia et al. |

FOREIGN PATENT DOCUMENTS

| WO | WO 96/05768 | 2/1996 |
|---|---|---|
| WO | WO 00/10456 | 3/2000 |
| WO | WO 01/06917 | 2/2001 |

* cited by examiner

*Primary Examiner*—Ruth S. Smith
(74) *Attorney, Agent, or Firm*—Mark M. Friedman (57) ABSTRACT

A method, and system for determining the position, and optionally, the orientation of a work piece such as a catheter within a cavity of an opaque body such as a patient. The position, and orientation are to be determined relative to a primary coordinate system, for example, the coordinate system of an imaging device. Using a primary reference transducer (210) that interacts with a primary field, and several secondary reference transducers (310) that interact with a secondary field, the coordinates of the secondary reference transducers are determined in the primary coordinate system.

39 Claims, 4 Drawing Sheets

LINKING OF AN INTRA-BODY TRACKING SYSTEM TO EXTERNAL REFERENCE COORDINATES

This application claims the benefit of Provisional Application No. 60/154,254, filed Sep. 16, 1999.

FIELD AND BACKGROUND OF THE INVENTION

The present invention relates to remote manipulation of a probe such as a catheter and, more particularly, to a method for determining the position and orientation, with respect to a coordinate system external to an opaque body, of a probe within the opaque body. Typically, the opaque body is a patient undergoing a medical procedure and the probe is a catheter.

Figure 1:
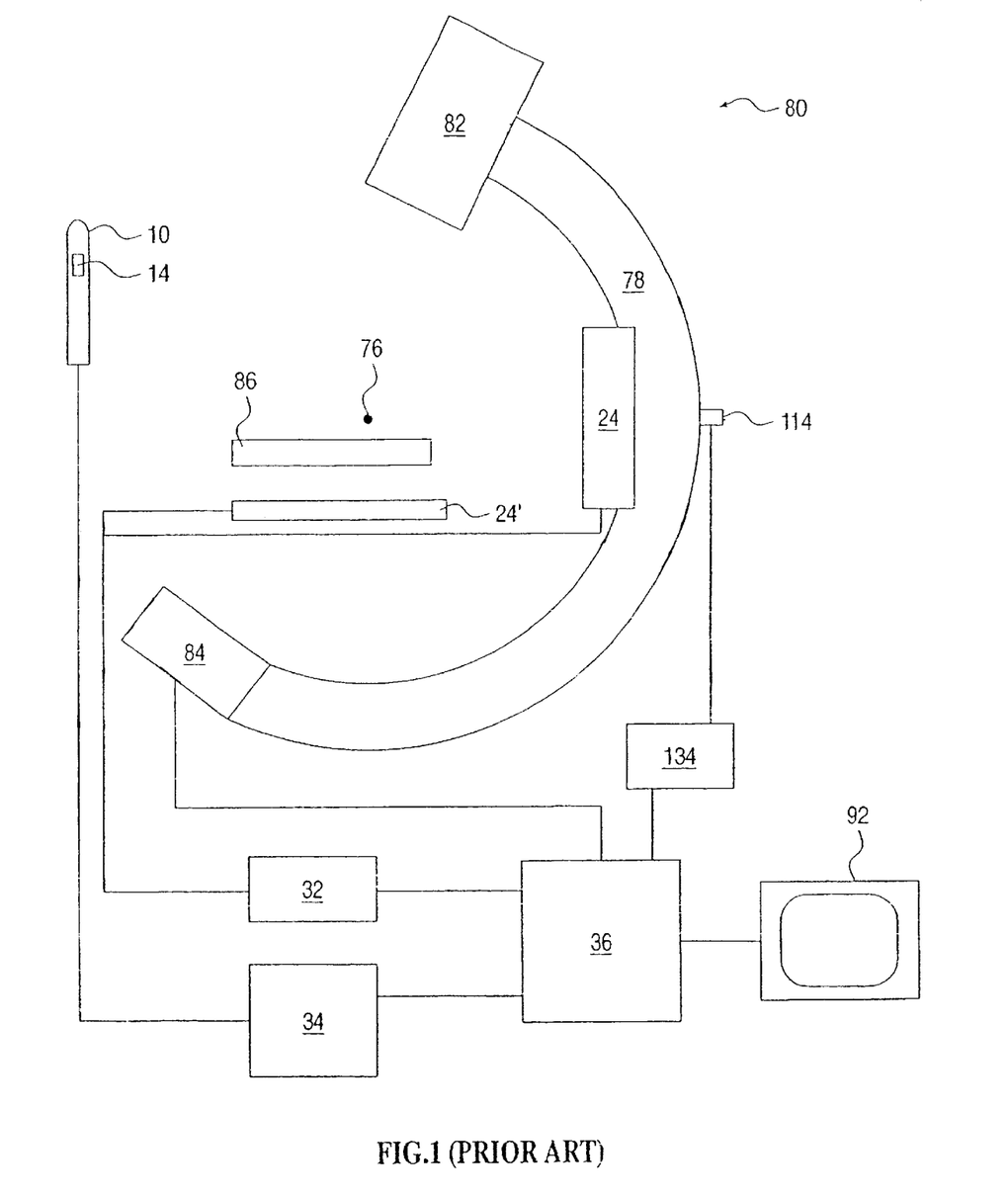
FIG. 1 shows a C-mount fluoroscope modified for real-time intrabody navigation according to the prior art.

It is known to navigate a catheter through body cavities of a patient by electromagnetic means. See, for example, U.S. Pat. No. 5,558,091, to Acker et al., PCT Application WO 96/05768, to Ben-Haim et al., and PCT Application IL99/00371. In particular, PCT Application IL99/00371, which is incorporated by reference for all purposes as if fully set forth herein, teaches devices and methods for navigating a catheter through body cavities of a patient while simultaneously obtaining, in real time, images of the portion of the patient through which the catheter is inserted, and superposing on the images a representation of the catheter in true position and orientation. FIG. 1 illustrates a C-mount fluoroscope 80 modified according to the teachings of IL99/00371 for simultaneous real-time image acquisition and intrabody navigation. Fluoroscope 80 includes the conventional components of a C-mount fluoroscope: an x-ray source 82 and an image acquisition module 84 mounted on opposite ends of a C-mount 78, and a table 86 whereon the patient lies. Image acquisition module 84 converts x-rays that transit the patient on table 86 into electronic signals representative of a 2D image of the patient. C-mount 78 is pivotable about an axis 76 to allow the imaging of the patient from several angles, thereby allowing the reconstruction of a 3D image of the patient from successive 2D images. In addition, either a three-component electromagnetic field receiver 114 or a three-component electromagnetic field transmitter 24 is rigidly mounted on C-mount 78. Receiver 114 or transmitter 24 serves to define a coordinate system that is fixed relative to C-mount 78. Transmitter 24, and another three-component electromagnetic field transmitter 24' that is not rigidly mounted on C-mount 78, are driven by driving circuitry 32. The electromagnetic waves generated by transmitter 24 or by transmitter 24' are received by receiver 114 and by another receiver 14 inside a probe 10. The signals from receiver 14 that correspond to the electromagnetic waves generated by transmitter 24 or by transmitter 24' are sent to reception circuitry 34. The signals from receiver 114 that correspond to the electromagnetic waves generated by transmitter 24 or by transmitter 24' are sent to reception circuitry 134. Reception circuitries 34 and 134 and driving circuitry 32 are controlled by a controller/processor 36 that directs the generation of transmitted signals by driving circuitry 32 and the reception of received signals by reception circuitries 34 and 134 In addition, controller processor 36 implements the algorithm of PCT IL99/00371 to infer the position and orientation of probe 10 relative to transmitter 24 or to infer the positions of probe 10 and receiver 114 relative to transmitter 24'. Controller/processor 36 also directs the acquisition of an image of the patient by image acquisition module 84 of fluoroscope 80.

By determining the position and orientation of probe 10 relative to the coordinate system defined by transmitter 24, controller/processor 36 determines the position and orientation of probe 10 relative to each acquired 2D image. Alternatively, the electromagnetic signals are transmitted by transmitter 24', and controller/processor 36 determines the position and orientation of probe 10 relative to the 2D images by determining the positions and orientations of receivers 14 and 114 relative to transmitter 24'. Controller/processor 36 synthesizes a combined image that includes both the 3D image of the patient acquired by fluoroscope 80 and an icon representing probe 10 positioned and oriented with respect to the 3D image of the patient in the same way as probe 10 is positioned and oriented with respect to the interior of the patient. Controller/processor 36 then displays this combined image on a monitor 92.

As noted in PCT IL99/00371, the methods taught therein for intrabody navigation are suitable for use in conjunction with a wide variety of devices for acquiring 2D or 3D images of the interior of the patient, in modalities including CT, MRI and ultrasound in addition to fluoroscopy.

Another family of systems, for determining the location of a probe such as a catheter within the body of a patient, uses a plurality of transducers on the surface of the patient's body and at least one similar transducer in the tip of the probe. The surface transducers define a reference system of coordinates. The signals produced by the various transducers are distinguishable from one another, and the character of the signals is diagnostic of the position on or within the patient's body at which the signals are received. Typically, either signals from the surface transducers are received by the probe transducers, or, exploiting the principal of reciprocity, signals from the probe transducers are received by the surface transducers. From these signals, the position of the tip of the probe relative to the reference coordinate system is determined. It should be noted that in this family of systems, the reference coordinate system, with respect to which the position of the probe is determined, is defined only with reference to the patient's body itself. This family of systems is incapable of determining the location of the probe with respect to a coordinate system external to, or independent of, the patient's body.

One example of such a system is taught by Smith et al. in U.S. Pat. No. 5,515,853, which is incorporated by reference for all purposes as if fully set forth herein. Ultrasonic signals are broadcast by a transducer (a piezoelectric crystal) at the tip of a catheter. These signals are received by a plurality of similar transducers on the patient's body, to measure the acoustic travel time from the tip of the catheter to the surface transceivers. The location of the tip of the catheter within the patient's body is determined by triangulation.

Another example of such a system is taught by Wittkampf in U.S. Pat. No. 5,697,377, incorporated by reference for all purposes as if fully set forth herein. Three substantially orthogonal alternating electrical currents, each of a different frequency, are applied through the patient's body via six electrodes mounted on the surface of the patient's body. A measuring electrode at the tip of a catheter measures the local electrical potential at each of the three frequencies. The displacement of the measuring electrode relative to lines connecting the pairs of surface electrodes is assumed to be linear in the three measured potentials. The surface electrodes define a (not necessarily orthogonal) reference coordinate system, and the three measured potentials are proportional to the coordinates of the measuring electrode in this coordinate system.

One drawback of the teachings of IL99/00371 is the relatively high cost and complexity of electromagnetic receivers 14 and 114 relative to the ultrasonic transceivers of Smith et al. and to the electrical transceivers of Wittkampf. It would be highly advantageous to have a method of intrabody navigation that relies on an electromagnetic technique to determine the position and orientation of the patient relative to the imaging device, while using some other technique, such as the ultrasonic technique of Smith et al. or the electrical technique of Wittkampf to determine the position and orientation of the probe relative to the patient's body.

DEFINITIONS

The term "transducer" usually is used to refer to a device that can interact with a physical field in either of two ways: by transmitting signals into the field or by receiving signals from the field. The piezoelectric crystals of Smith et al. are examples of transducers that interact in this manner with an acoustic field. The electrodes of Wittkampf are examples of transducers that interact in this manner with an electric potential field. As used herein, the term "transducer" also includes devices that interact with a physical field only by transmitting signals into the field and devices that interact with a physical field only by receiving signals from the field. The term "transducer", as used herein, thus includes within its scope receivers 14 and 114 that are used only for reception of electromagnetic signals and not for transmission of electromagnetic signals. It should be noted that receivers 14 and 114 typically include wire coils that could be used either for transmission or for reception, but the small dimensions of probe 10 preclude the application of sufficiently high power levels to the coils of receiver 14 to allow receiver 14 to be used for transmission.

Note that the field with which the transceiver interacts may be a scalar field, such as the acoustic field of Smith et al. or the electric potential field of Wittkampf, or may be a vector field such as the electromagnetic field of PCT IL99/00371.

Two or more transducers are said to have a "fixed spatial relationship" to each other if the transducers are deployed so that their only allowed movements are collective translations or collective rigid rotations. In the preferred embodiments discussed below, transducers are provided with fixed spatial relationships to each other by being attached rigidly to a common substrate such as a catheter. Similarly, a transducer is said to have a "fixed spatial relationship" to another body (e.g., a the body of a patient) if the transducers are attached to the body so that as the body moves, the position and orientation of the transducer mimics or reflects the position and orientation of the moving body.

SUMMARY OF THE INVENTION

According to the present invention there is provided a method for determining a position and an orientation of a workpiece relative to a primary coordinate system, including the steps of: (a) providing a primary reference transducer that interacts with a primary field; (b) providing a plurality of secondary reference transducers that interact with a secondary field different from the primary field, the secondary transducers being in a fixed mutual spatial relationship so as to define a secondary coordinate system, the primary reference transducer being in a fixed spatial relationship to the secondary transducers; (c) measuring at least one value of the primary field, using the primary reference transducer; (d) inferring, from the at least one value of the primary field, a position and an orientation of the reference transducers relative to the primary coordinate system, thereby determining a position and an orientation of the secondary coordinate system relative to the primary coordinate system; (e) providing the workpiece with at least one workpiece transducer that interacts with the secondary field; (f) measuring a plurality of values of the secondary field, using the secondary reference transducers and the workpiece transducer; (g) inferring, from the values of the secondary field, a first measure of a position of the workpiece relative to the secondary coordinate system; and (h) combining the first measure of the position of the workpiece relative to the secondary coordinate system with the position and the orientation of the secondary coordinate system relative to the primary coordinate system to provide the position and the orientation of the workpiece relative to the primary coordinate system.

According to the present invention there is provided a method of navigating a probe inside a body, including the steps of: (a) providing a primary reference transducer that interacts with a primary field; (b) providing a plurality of secondary reference transducers that interact with a secondary field different from the primary field, the secondary transducers being in a fixed mutual spatial relationship and in a fixed spatial relationship to the body, the primary reference transducer being in a fixed spatial relationship to the secondary transducers; (c) providing a device for acquiring an image of the body; (d) simultaneously: (i) acquiring the image of the body, (ii) measuring at least one value of the primary field; using the primary reference transducer, and (iii) inferring, from the at least one value of the primary field, a position and an orientation of the reference transducers relative to the device, thereby determining a position and an orientation of the body relative to the image; (e) determining a position of the probe relative to the body by: (i) providing the probe with at least one probe transducer that interacts with the secondary field; (ii) measuring a plurality of values of the secondary field, using the secondary reference transducers and the probe transducer, and (iii) inferring, from the values of the secondary field, the position of the probe relative to the body; and (f) displaying the image of the body with a representation of the probe superposed thereon according to the positions and the orientation.

According to the present invention there is provided a system for navigating a probe through an opaque body, including: (a) a primary reference transducer that interacts with a primary field; (b) a plurality of secondary reference transducers that interact with a secondary field; (c) a mechanism for deploying the reference transducers in a fixed mutual spatial relationship; and (d) at least one probe transducer, having a fixed spatial relationship to the probe, that interacts with the secondary field.

According to the present invention there is provided a method for determining a position and an orientation of a first workpiece relative to both a second workpiece and a primary coordinate system, including the steps of: (a) providing the second workpiece with at least one primary transducer that interacts with a primary field and that defines a workpiece coordinate system that is fixed with respect to the second workpiece; (b) providing a mechanism for generating a secondary field and for defining a secondary coordinate system; (c) providing the first workpiece with at least one secondary transducer that interacts with the secondary field; (d) providing a transformation from the secondary coordinate system to the workpiece coordinate system; (e) measuring at least one value of the secondary field, using the at least one workpiece transducer; (f) inferring, from the at least one value of the secondary field, a position of the first workpiece relative to the secondary coordinate system; (g) measuring at least one value of the primary field, using the at least one primary transducer; (h) inferring, from the at least one value of the primary field, a position and an orientation of the at least one reference transducer relative to the primary coordinate system, thereby providing a transformation from the workpiece coordinate system to the primary coordinate system; (i) combining the position of the first workpiece relative to the secondary coordinate system with the transformation from the secondary coordinate system to the workpiece coordinate system to provide the position and the orientation of the first workpiece relative to the second workpiece; and (j) combining the position and the orientation of the first workpiece relative to the second workpiece with the transformation from the workpiece coordinate system to the primary coordinate system to provide the position and the orientation of the first workpiece relative to the primary coordinate system.

According to the present invention there is provided a method of navigating a probe inside a body, including the steps of: (a) providing a device for acquiring an image of the body; (b) providing the body with at least one body transducer that is in a fixed spatial relationship to the body and that interacts with a primary field; (c) simultaneously: (i) acquiring the image of the body, (ii) measuring at least one value of the primary field, using the at least one body transducer, and (iii) inferring, from the at least one value of the primary field, a position and an orientation of the at least one body transducer relative to the device, thereby determining a position and an orientation of the body relative to the image; (d) determining a position of the probe relative to the body by: (i) providing the probe with at least one probe transducer that interacts with a secondary field; (ii) measuring a plurality of values of the secondary field, using the at least one probe transducer, and (iii) inferring, from the values of the secondary field, the position of the probe relative to the body; and (e) displaying the image of the body with a representation of the probe superposed thereon according to the positions and the orientation.

According to the present invention there is provided a system for navigating a probe through an opaque body, including: (a) at least one primary transducer that interacts with a primary field; (b) a generating mechanism for generating a secondary field; (c) a securing mechanism for securing the at least one primary transducer and the generating mechanism in a fixed spatial relationship to the opaque body; and (d) at least one probe transducer, having a fixed spatial relationship to the probe, that interacts with the secondary field.

In the context of intrabody navigation, the imaging device defines a primary coordinate system, and the physical field that is used to determine positions and orientations relative to the imaging device is considered to be a primary field. For example, in the prior art system of FIG. 1, the primary field is an electromagnetic field, and receiver 14 interacts with the primary field. According to the present invention, receiver 14 is replaced with one or more transducers of a secondary field. According to one aspect of the present invention, the patient is provided with a plurality of secondary reference transducers that also interact with the secondary field and with a primary reference transducer that interacts with the primary field. The reference transducers are in mutual fixed spatial relationship, typically by being rigidly attached to a reference probe that is inserted into the body cavity along with probe 10. The secondary reference transducers define a secondary coordinate system for determining positions and optionally orientations relative to the patient's body. The primary reference transducer is used to determine the position and orientation of the secondary coordinate system of the patient's body, with respect to the primary coordinate system of the imaging device. The secondary reference transducers are used along with the transducers that replace receiver 14 to determine the position and optionally the orientation of probe 10 relative to the secondary coordinate system. The positions and orientation or orientations thus determined are combined by well-known methods to provide the position, and optionally the orientation, of probe 10 relative to the images provided by the imaging device.

According to a second aspect of the present invention, the mechanism for generating the secondary field itself defines the secondary coordinate system. Under this aspect of the present invention, which lacks the reference probe, one or more primary transducers are attached to the patient's body to provide a body coordinate system. For calibration, the catheter is provided with a calibration transducer, having a fixed spatial relationship to the secondary field transducers, that also interacts with the primary field. Simultaneous measurements of the catheter position with respect to the body, using the primary transducers and the calibration transducer, provides a transformation from secondary coordinates to body coordinates. During the calibration, the body coordinates coincide with the secondary coordinates. Subsequently, field measurements made using the primary transducers provide transformations from body coordinates to primary coordinates, and the two transformations are combined to provide the position and the orientation of the catheter in primary coordinates.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of a method of determining the position and orientation of a probe within an opaque body. Specifically, the present invention can be used to navigate a catheter through the body cavities of a patient in real time.

The principles and operation of intrabody navigation according to the present invention may be better understood with reference to the drawings and the accompanying description.

Figure 2:
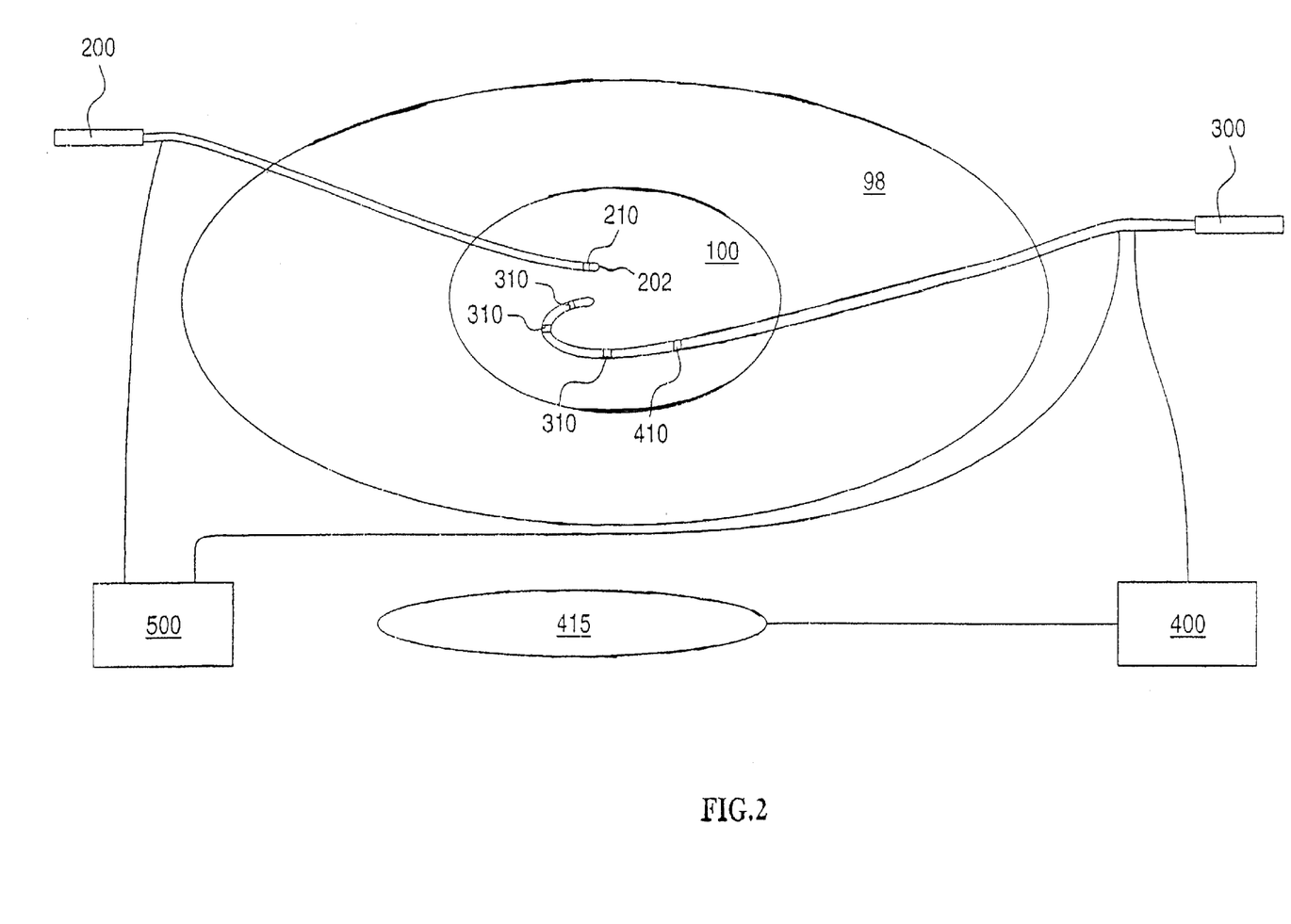
FIG. 2 is a schematic diagram of a system of the present invention.

Referring now to the drawings, FIG. 2 is a schematic diagram of a system of the present invention. A catheter 200 is inserted in a cavity 100 of a patient 98. It is desired to measure the position of tip 202 of catheter 200, in three dimensions, relative to an external primary orthogonal coordinate system, typically a coordinate system defined by an imaging device such as C-mount fluoroscope 80 of FIG. 1. For this purpose, a catheter transducer 210 is integrated into tip 202 of catheter 200. A reference catheter 300 also is inserted into cavity 100. Rigidly attached to catheter 300 are at least three reference transducers 310, and also an electromagnetic sensor 410, similar to receiver 14, that senses the three components of an electromagnetic field generated by a set 415 of antennas. Sensor 410 and antennas 415 are controlled by an electromagnetic locator system 400 of the type taught in PCT IL99/00371, as described above: antennas 415 are similar to transmitters 24 and 24' described above, and locator system 400 includes hardware that is functionally equivalent to driving circuitry 32, reception circuitry 34 and controller/processor 36 discussed above. Locator system 400 is operative to measure the location and orientation of sensor 410, and so of catheter 300, relative to the external primary orthogonal coordinate system. Transducers 210 and 310 all transmit and/or receive the same kind of nonelectromagnetic signals, as described below. Transducers 210 and 310 are operated together for this purpose using a nonelectromagnetic localization system 500.

In one preferred embodiment of the present invention, nonelectromagnetic localization system 500 is an ultrasonic localization system similar to the one described by Smith et al. Transducer 210 is an ultrasonic transmitter and transducers 310 are ultrasonic receivers which preferably all have the same resonance frequency. Reference transducers 310 should not be collinear, so that reference transducers 310 define a plane that, along with the normal to the plane, define an orthogonal secondary coordinate system. Because sensor 410 is rigidly attached to catheter 300, sensor 410 and electromagnetic locator system 400 can be used to determine the position and orientation of the secondary coordinate system relative to the primary coordinate system. Using localization system 500, the distances from transducer 210 to transducers 310 are measured. The location of transducer 210 in the secondary coordinate system is determined by triangulation, and this location is transformed to an equivalent location in the primary coordinate system.

Figure 3:
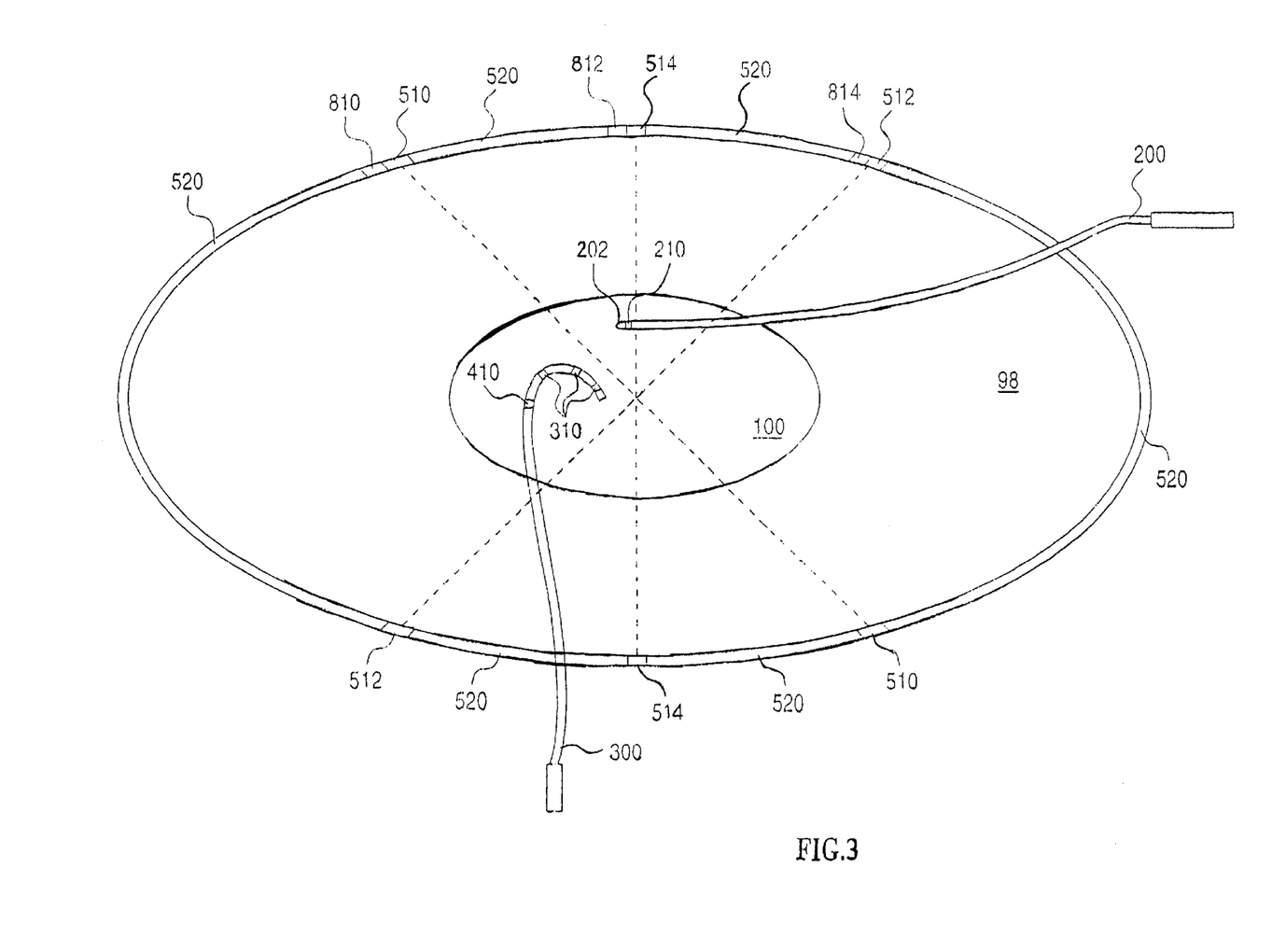
FIG. 3 is a partial schematic illustration of a second embodiment of the present invention.

In another preferred embodiment of the present invention, nonelectromagnetic localization system 500 is an electrical localization system similar to that of Wittkampf. FIG. 3 is a partial schematic illustration of this embodiment. Pairs 510, 512 and 514 of electrodes are attached to the surface of the body of patient 98. System 500 transmits an alternating current between the members of each pair of electrodes, with each pair receiving an alternating current of a different frequency or phase, so that three superposed but distinguishable electrical potential fields are formed within the body of patient 98. Transducers 210 and 310 are electrodes for measuring the local electrical potentials relative to ground. Alternatively, the electrical potentials of electrodes 310 are measured relative to electrode 210. These potentials vary linearly with the translational position of electrodes 210 and 310 within cavity 100. Given the coefficients of this linear variation, the potential measurements provide a measure of the distances from transducer 210 to transducers 310. In all other respects, the operation of the second preferred embodiment is identical to the operation of the first preferred embodiment: the location of transducer 210 in the secondary coordinate system defined by transducers 310 is found by triangulation, and this location is transformed to an equivalent location in the primary coordinate system.

Alternatively, the coordinate system defined by electrode pairs 510, 512 and 514 is used as the secondary coordinate system. The coordinate axes of this alternative secondary coordinate system are indicated in FIG. 3 as dashed lines connecting the members of the electrode pairs. Under this alternative, one or more external reference electromagnetic sensors are used instead of reference transducers 310 and 410. Three such electromagnetic sensors 810, 812 and 814 are shown in FIG. 3. Electrode pairs 510, 512 and 514 and sensors 810, 812 and 814 are secured in a fixed spatial relationship to body 98 by straps 520.

Figure 4:
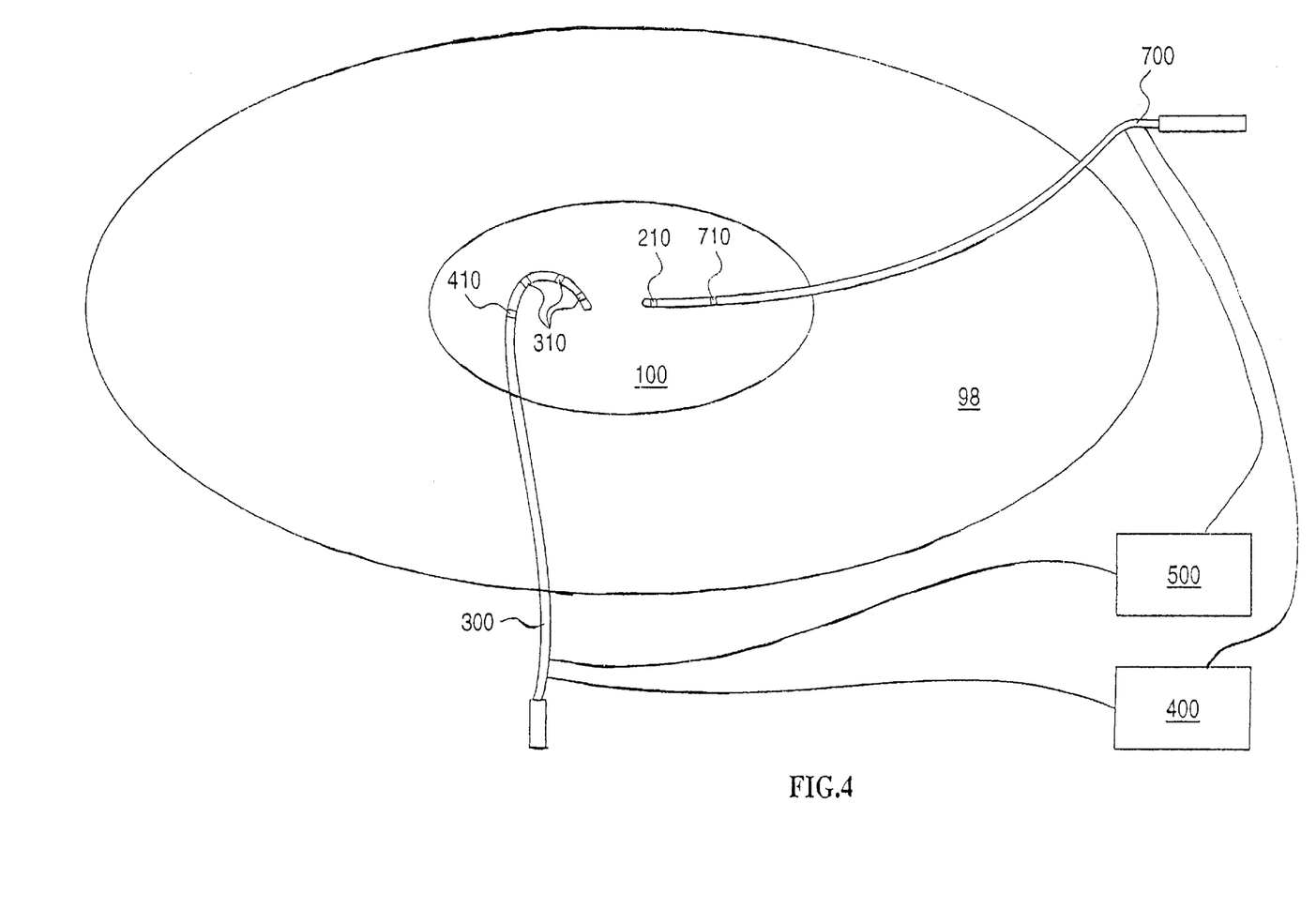
FIG. 4 illustrates the calibration procedure of the present invention.

Preferably, the systems of both preferred embodiments are calibrated before being used to measure the location of tip 202. FIG. 4 illustrates the calibration procedure. Catheter 200 is replaced with a calibration catheter 700 that includes, in addition to transducer 210, an electromagnetic sensor 710 that is operationally connected to electromagnetic locator system 400. The displacement between sensor 710 and transducer 210 along catheter 700 is known, so the measurements taken with sensor 710 provide the location of transducer 210 in the primary coordinate system. For redundancy, the tip of catheter 700 is moved among several locations in cavity 100, and the locations of transducers 210 and 310 are measured using both electromagnetic locator system 400 and nonelectromagnetic localization system 500. These measurements provide enough information to determine a transformation from the secondary coordinate system to the primary coordinate system.

If the secondary coordinate system is orthogonal, then the transformation to primary coordinates is a composition of a rotation and a translation. In general, however, the secondary coordinate system, as defined by transducers 310 or by electrode pairs 510, 512 and 514, is nonorthogonal. For example, in the ultrasonic embodiment, the delays measured between ultrasonic transmitter 210 and ultrasonic receivers 310 include both the actual propagation times from transmitter 210 to receivers 310 and additional delays associated with the transfer functions of the piezoelectric crystals of receivers 310 and with the associated electronic circuitry. In the case of the electrical embodiment, electrode pairs 510, 512 and 514 usually define a nonorthogonal coordinate system and an anisotropic electrical potential field. Therefore, in general, the transformation from the secondary coordinate system to the primary coordinate system is a composition of a nonorthogonal transformation (the product of the secondary Cartesian coordinate vector with a general 3×3 matrix) and a translation. At least four independent simultaneous measurements of the positions of transducers 210 and 310 are needed to determine this transformation. Each simultaneous measurement provides three equations in the twelve unknowns (nine matrix elements and three components of the translation vector). Preferably, more than four independent simultaneous measurements of the positions of transducers 210 and 310 are made, and the twelve unknowns are fitted to the calibration measurements in a least squares sense.

It will be appreciated that by including two or more transducers 210 in catheter 200, some or all of the components of the orientation of catheter 200 in the primary coordinate system may be determined in addition to the location of tip 202.

In the alternative electrical embodiment, in which electrodes 310 are not used and the secondary coordinate system is defined by electrode pairs 510, 512 and 514, the minimal calibration consists of moving the tip of catheter 700 to four different calibration positions, for example, the corners of a tetrahedron. At each position, sensor 710 is used to determine the coordinates of electrode 210 in the primary (electromagnetic) coordinate system. The potentials of electrode 210 relative to ground, at the three frequencies associated with electrode pairs 510, 512 and 514, are the coordinates of electrode 210 in the secondary (electrical) coordinate system. As before, these four measurements suffice, in principle, to determine the transformation from secondary coordinates to primary coordinates. Also as before, it is preferable to move the tip of catheter 700 to more than four different calibration positions and to fit the twelve parameters of the transformation to the calibration measurements in a least squares sense.

In practice, patient 98 may move between the calibration with catheter 700 and the measurements with catheter 200. In the electrical embodiment that employs reference catheter 300 and reference electrodes 310, this, movement of patient 98 does not matter because reference catheter 300 provides a frame of reference that is fixed with respect to patient 98. In the alternative electrical embodiment that does not employ reference catheter 300 and reference electrodes 310 and 410, reference electromagnetic sensors 810, 812 and 814, that are similar to electromagnetic sensor 410, are attached to the surface of the body of patient 98 along with electrode pairs 510, 512 and 514 to provide a body coordinate system that is fixed with respect to the body of patient 98. During calibration, the body and primary coordinate systems coincide, and the calibration procedure provides the transformation from the secondary coordinate system to the body coordinate system. After patient 98 moves, the positions and orientations of sensors 810, 812 and 814, as measured by electromagnetic locator system 400, provide the transformation from the body coordinate system to the primary coordinate system. In principle, only one sensor 810, 812 or 814 is needed for these measurements. In practice, several such sensors are used, as illustrated, for redundancy.

While the invention has been described with respect to a limited number of embodiments, it will be appreciated that many variations, modifications and other applications of the invention may be made.

What is claimed is:

1. A method for determining a position and an orientation of a workpiece relative to a primary coordinate system, comprising the steps of:
   (a) providing a primary reference transducer that interacts with a primary field;
   (b) providing a plurality of secondary reference transducers that interact with a secondary field different from said primary field, said secondary transducers being in a fixed mutual spatial relationship so as to define a secondary coordinate system, said primary reference transducer being in a fixed spatial relationship to said secondary transducers;
   (c) measuring at least one value of said primary field, using said primary reference transducer;
   (d) inferring, from said at least one value of said primary field, a position and an orientation of said reference transducers relative to the primary coordinate system, thereby determining a position and an orientation of said secondary coordinate system relative to the primary coordinate system;
   (e) providing the workpiece with at least one workpiece transducer that interacts with said secondary field;
   (f) measuring a plurality of values of said secondary field, using said secondary reference transducers and said workpiece transducer;
   (g) inferring, from said values of said secondary field, a first measure of a position of the workpiece relative to said secondary coordinate system; and
   (h) combining said first measure of said position of the workpiece relative to said secondary coordinate system with said position and said orientation of said secondary coordinate system relative to the primary coordinate system to provide the position and the orientation of the workpiece relative to the primary coordinate system.

2. The method of claim 1, wherein said primary field is a vector field.

3. The method of claim 2, wherein said primary field is an electromagnetic field.

4. The method of claim 1, wherein said secondary field is a scalar field.

5. The method of claim 4, wherein said secondary field is an acoustic field.

6. The method of claim 5, wherein each of said secondary reference transducers and each of said at least one workpiece transducer includes a piezoelectric crystal.

7. The method of claim 4, wherein said secondary field is an electric potential field.

8. The method of claim 7, wherein each of said secondary reference transducers and each of said at least one workpiece transducer includes an electrode.

9. The method of claim 1, further comprising the step of:
   (i) calibrating said inferring of said first measure of said position of the workpiece.

10. The method of claim 9, wherein said calibrating includes the steps of:
    (i) providing the workpiece with at least one calibration transducer that interacts with said primary field and that is in a fixed spatial relationship to said at least one workpiece transducer,
    (ii) measuring at least one value of said primary field, using said calibration transducer, and
    (iii) inferring, from said at least one value of said primary field, a position and an orientation of the workpiece relative to said primary coordinate system.

11. The method of claim 10, wherein said calibrating further includes the step of:
    (iv) inferring, from said position and said orientation of the workpiece relative to said primary coordinate system, and from said position and said orientation of said secondary coordinate system relative to the primary coordinate system, a second measure of said position of the workpiece relative to said secondary coordinate system.

12. The method of claim 1, wherein the workpiece is provided with a plurality of said workpiece transducers, the method further comprising the step of:
    (i) inferring, from said values of said secondary field, an orientation of the workpiece relative to said secondary coordinate system.

13. A method of navigating a probe inside a body, comprising the steps of:
    (a) providing a primary reference transducer that interacts with a primary field;
    (b) providing a plurality of secondary reference transducers that interact with a secondary field different from said primary field, said secondary transducers being in a fixed mutual spatial relationship and in a fixed spatial relationship to the body, said primary reference transducer being in a fixed spatial relationship to said secondary transducers;
    (c) providing a device for acquiring an image of the body;
    (d) simultaneously:
       (i) acquiring said image of the body,
       (ii) measuring at least one value of said primary field, using said primary reference transducer, and
       (iii) inferring, from said at least one value of said primary field, a position and an orientation of said reference transducers relative to the device, thereby determining a position and an orientation of the body relative to the image;

(e) determining a position of the probe relative to the body by:
  (i) providing the probe with at least one probe transducer that interacts with said secondary field;
  (ii) measuring a plurality of values of said secondary field, using said secondary reference transducers and said probe transducer, and
  (iii) inferring, from said values of said secondary field, said position of the probe relative to the body; and
(f) displaying said image of the body with a representation of the probe superposed thereon according to said positions and said orientation.

14. The method of claim 13, wherein said primary field is a vector field.

15. The method of claim 14, wherein said primary field is an electromagnetic field.

16. The method of claim 13, wherein said secondary field is a scalar field.

17. The method of claim 16, wherein said secondary field is an acoustic field.

18. The method of claim 17, wherein each of said secondary reference transducers and each of said at least one probe transducer includes a piezoelectric crystal.

19. The method of claim 16, wherein said secondary field is an electric potential field.

20. The method of claim 19, wherein each of said secondary reference transducers and each of said at least one probe transducer includes an electrode.

21. The method of claim 13, wherein said image is selected form the group of modalities consisting of CT, MRI, ultrasound and fluoroscopy.

22. A system for navigating a probe through an opaque body, comprising:
  (a) a primary reference transducer that interacts with a primary field;
  (b) a plurality of secondary reference transducers that interact with a secondary field, said secondary field being an electric potential field;
  (c) a mechanism for deploying said reference transducers in a fixed mutual spatial relationship; and
  (d) at least one probe transducer, having a fixed spatial relationship to the probe, that interacts with said secondary field,
  wherein each of said secondary reference transducers and each of said at least one probe transducer includes an electrode.

23. The system of claim 22, wherein said mechanism includes a reference object to which said reference transducers are rigidly attached.

24. The system of claim 22, wherein said at least one probe transducer is rigidly attached to said probe.

25. The system of claim 22, further comprising:
  (e) at least one calibration transducer that interacts with said primary field and that has a fixed spatial relationship to said at least one probe transducer.

26. A method for determining a position and an orientation of a first workpiece relative to both a second workpiece and a primary coordinate system, comprising the steps of:
  (a) providing the second workpiece with at least one primary transducer that interacts with a primary field and that defines a workpiece coordinate system that is fixed with respect to the second workpiece;
  (b) providing a mechanism for generating a secondary field and for defining a secondary coordinate system;
  (c) providing the first workpiece with at least one secondary transducer that interacts with said secondary field;
  (d) providing a transformation from said secondary coordinate system to said workpiece coordinate system;
  (e) measuring at least one value of said secondary field, using said at least one secondary transducer;
  (f) inferring, from said at least one value of said secondary field, a position of the first workpiece relative to said secondary coordinate system;
  (g) measuring at least one value of said primary field, using said at least one primary transducer:
  (h) inferring, from said at least one value of said primary field, a position and an orientation of said at least one primary transducer relative to the primary coordinate system, thereby providing a transformation from said workpiece coordinate system to the primary coordinate system;
  (i) combining said position of the first workpiece relative to said secondary coordinate system with said transformation from said secondary coordinate system to said workpiece coordinate system to provide the position and the orientation of the first workpiece relative to the second workpiece; and
  (j) combining the position and the orientation of the first workpiece relative to the second workpiece with said transformation from said workpiece coordinate system to the primary coordinate system to provide the position and the orientation of the first workpiece relative to the primary coordinate system.

27. The method of claim 26, wherein said primary field is a vector field.

28. The method of claim 27, wherein said primary field is an electromagnetic field.

29. The method of claim 28, wherein said secondary field is a scalar field.

30. The method of claim 29, wherein said secondary field is an electric potential field.

31. The method of claim 30, wherein each of said at least one workpiece transducer includes an electrode.

32. The method of claim 26, wherein said providing of said transformation from said secondary coordinate system to said workpiece coordinate system includes the steps of:
  (i) providing the first workpiece with at least one calibration transducer that interacts with said primary field and that is in a fixed spatial relationship to said at least one workpiece transducer;
  (ii) simultaneously measuring a plurality of values of said primary field, using said at least one primary transducer and said calibration transducer; and
  (iii) inferring, from said simultaneously measured plurality of values of said primary field, positions and orientation of both workpieces with respect to the primary field.

33. A method of navigating a probe inside a body, comprising the steps of:
  (a) providing a device for acquiring an image of the body;
  (b) providing the body with at least one body transducer that is in a fixed spatial relationship to the body and that interacts with a primary field;
  (c) simultaneously:
    (i) acquiring said image of the body,
    (ii) measuring at least one value of said primary field, using said at least one body transducer, and
    (iii) inferring, from said at least one value of said primary field, a position and an orientation of said at least one body transducer relative to the device, thereby determining a position and an orientation of the body relative to the image;

(d) determining a position of the probe relative to the body by:
   (i) providing the probe with at least one probe transducer that interacts with a secondary field;
   (ii) measuring a plurality of values of said secondary field, using said at least one probe transducer, and
   (iii) inferring, from said values of said secondary field, said position of the probe relative to the body; and
(e) displaying said image of the body with a representation of the probe superposed thereon according to said positions and said orientation.

34. The method of claim 33, wherein said primary field is a vector field.

35. The method of claim 34 wherein said primary field is an electromagnetic field.

36. The method of claim 33, wherein said secondary field is a scalar field.

37. The method of claim 36, wherein said secondary field is an electric potential field.

38. The method of claim 37, wherein each of said probe transducers includes an electrode.

39. The method of claim 33, wherein said image is selected from the group of modalities consisting of CT, MRI, ultrasound and fluoroscopy.

* * * * *